United States Patent
Lv et al.

(10) Patent No.: US 10,940,328 B2
(45) Date of Patent: Mar. 9, 2021

(54) IRRADIATION DEVICE AND METHOD FOR USING THE SAME

(71) Applicant: BOE TECHNOLOGY GROUP CO., LTD., Beijing (CN)

(72) Inventors: Xuewen Lv, Beijing (CN); Junyuan Ren, Beijing (CN); Jie Lin, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 626 days.

(21) Appl. No.: 15/742,387

(22) PCT Filed: Apr. 19, 2017

(86) PCT No.: PCT/CN2017/081024
§ 371 (c)(1),
(2) Date: Jan. 5, 2018

(87) PCT Pub. No.: WO2017/193776
PCT Pub. Date: Nov. 16, 2017

(65) Prior Publication Data
US 2018/0193662 A1    Jul. 12, 2018

(30) Foreign Application Priority Data
May 12, 2016   (CN) .......................... 201610317694.0

(51) Int. Cl.
*A61N 5/06* (2006.01)
*A61B 5/00* (2006.01)

(52) U.S. Cl.
CPC .......... *A61N 5/0616* (2013.01); *A61B 5/0077* (2013.01); *A61B 5/441* (2013.01);
(Continued)

(58) Field of Classification Search
CPC combination set(s) only.
See application file for complete search history.

(56) References Cited

U.S. PATENT DOCUMENTS

2003/0045916 A1    3/2003   Anderson et al.
2008/0051773 A1*   2/2008   Ivanov .................. A61N 5/0616
                                                                606/12
(Continued)

FOREIGN PATENT DOCUMENTS

CN    102861379 A    1/2013
CN    103298524 A    9/2013
(Continued)

OTHER PUBLICATIONS

First Chinese Office Action, for Chinese Patent Application No. 201610317694.0, dated Jan. 2, 2018, 17 pages.
(Continued)

*Primary Examiner* — Scott Luan
(74) *Attorney, Agent, or Firm* — Kinney & Lange, P.A.

(57) ABSTRACT

An irradiation device comprises a light source, an optical switch element and an image recognition module communicatively connected to the optical switch element. In some embodiments, a contour of a target area is recognized by an image recognition module and is provided by the image recognition module to the optical switch element, and a contour of an irradiation area of the light source is controlled by the optical switch element to match with the contour of the target area according to the contour of the target area provided by the image recognition module. Thus, when skin diseases are treated using the irradiation device according to some embodiments of the present disclosure, the contour of the irradiation area of the light source coincides with the contour of the target area, thereby ensuring a therapeutic effect with respect to the target area while avoiding damages to skin in a healthy area.

13 Claims, 9 Drawing Sheets

(52) U.S. Cl.
    CPC ............... *A61N 5/06* (2013.01); *A61B 5/444* (2013.01); *A61B 2562/0242* (2013.01); *A61N 2005/0626* (2013.01); *A61N 2005/0642* (2013.01); *A61N 2005/0659* (2013.01); *A61N 2005/0661* (2013.01); *A61N 2005/0662* (2013.01); *A61N 2005/0667* (2013.01)

(56) References Cited

U.S. PATENT DOCUMENTS

| | | | |
|---|---|---|---|
| 2009/0143842 A1* | 6/2009 | Cumbie | ............... A61N 5/0624 607/88 |
| 2013/0231720 A1 | 9/2013 | Luellau | |
| 2016/0101294 A1 | 4/2016 | Sun et al. | |

FOREIGN PATENT DOCUMENTS

| | | | |
|---|---|---|---|
| CN | 103920248 | A | 7/2014 |
| CN | 104740786 | A | 7/2015 |
| CN | 105363132 | A | 3/2016 |
| CN | 106039579 | A | 10/2016 |
| CN | 205729993 | A | 11/2016 |
| CN | 205729993 | U | 11/2016 |

OTHER PUBLICATIONS

International Search Report & Box V of Written Opinion, for PCT Patent Application No. PCT/CN2017/081024, dated Jul. 13, 2017, 17 pages.
First Chinese Office Action dated Sep. 18, 2018, received for corresponding Chinese Application No. 201610317694.0.

\* cited by examiner

IRRADIATION DEVICE AND METHOD FOR USING THE SAME

CROSS-REFERENCE TO RELATED APPLICATION(S)

This application is a U.S. National Phase Application of International Application No. PCT/CN2017/081024, filed on Apr. 19, 2017, entitled "IRRADIATION DEVICE AND METHOD FOR USING THE SAME," which claims priority to the Chinese Application No. 201610317694.0, filed on May 12, 2016, both of which are incorporated herein by reference in their entireties.

TECHNICAL FIELD

The present disclosure relates to the field of irradiation devices, and more particularly, to an irradiation device and a method for using the same.

BACKGROUND

The ultraviolet therapy in dermatology is a physical treatment technology which irradiates human skin using ultraviolet light for treatment of skin diseases. Currently, human skin is directly irradiated using an ultraviolet light source during the treatment of skin diseases through the ultraviolet therapy.

As the human skin has areas to be treated in diversified shapes, a shape of an irradiation area of an existing ultraviolet light source on the human skin is usually in a regular geometrical shape, such as a circle or a square. When the irradiation area of the ultraviolet light source on the human skin exceeds an area to be treated on the human skin, ultraviolet irradiation may damage human skin in a healthy area, and when the irradiation area of the ultraviolet light source on the human skin cannot cover the area to be treated on the human skin, a part of the area to be treated which is not irradiated cannot be effectively treated, which results in a poor therapeutic effect.

SUMMARY

According to an aspect of the present disclosure, there is provided an irradiation device, comprising: a body of the irradiation device, a light source located on the body of the irradiation device, an optical switch element and an image recognition module communicatively connected to the optical switch element, wherein the image recognition module is configured to recognize a contour of an area to be treated and provide the contour of the area to be treated to the optical switch element, and the optical switch element controls a contour of an irradiation area formed by irradiation of the light source on the area to be treated to match with the contour of the area to be treated provided by the image recognition module.

According to another aspect of the present disclosure, there is provided a method for using an irradiation device, comprising steps of:

recognizing, by an image recognition module, a contour of an area to be treated and providing the contour of the area to be treated to an optical switch element; and controlling, by the optical switch element, a contour of an irradiation area formed by irradiation of the light source on the area to be treated to match with the contour of the area to be treated.

BRIEF DESCRIPTION OF THE DRAWINGS

In order to describe the technical solutions according to the embodiments of the present disclosure more clearly, the accompanying drawings required for describing the embodiments will be described briefly below. It is obvious that the accompanying drawings in the following description are merely some embodiments of the present disclosure, and other accompanying drawings can further be obtained by those of ordinary skill in the art according to these accompanying drawings without contributing any creative work.

Figure 1:
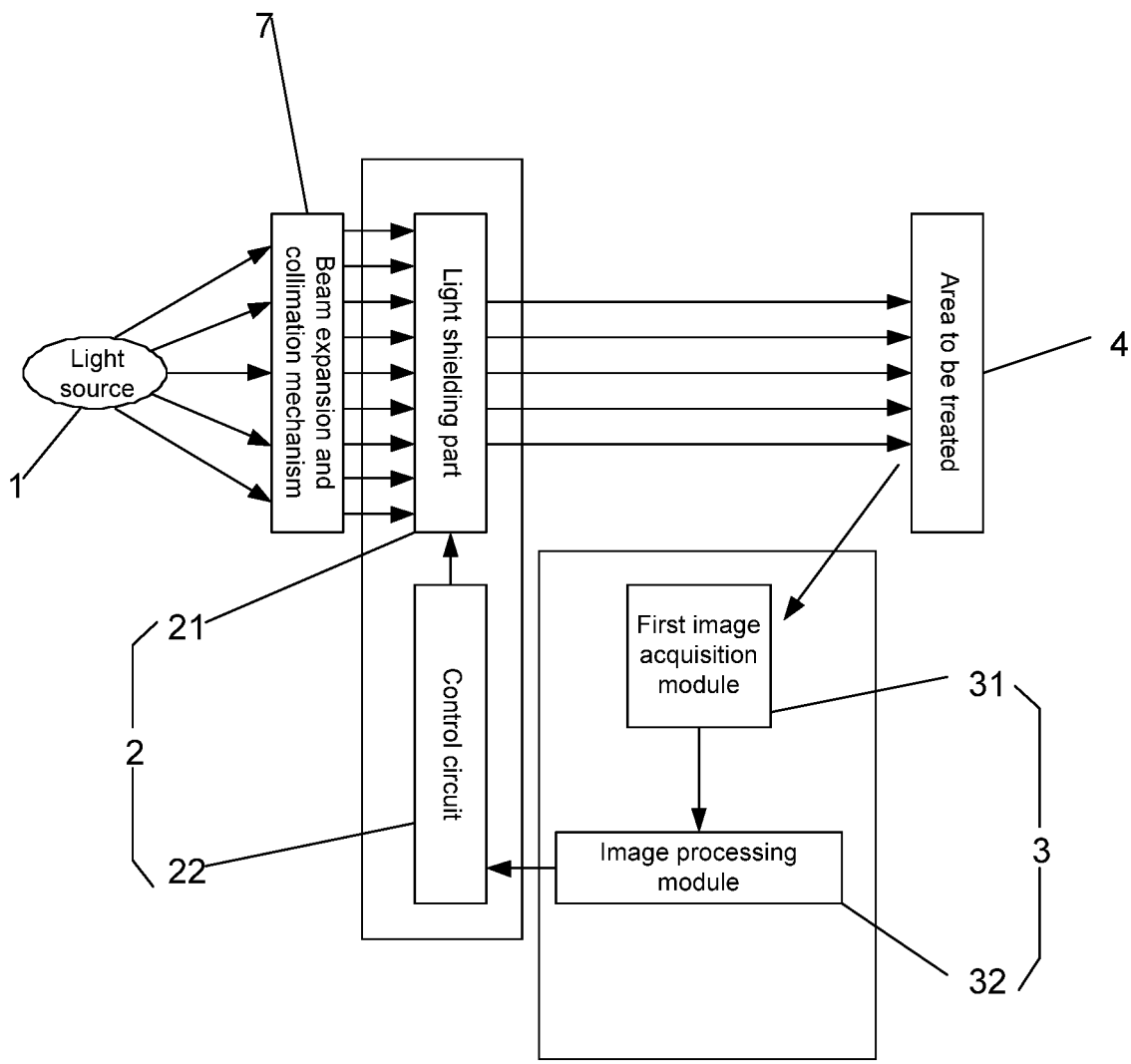
FIG. 1 is a structural diagram of an irradiation device according to an embodiment of the present disclosure.

In the accompanying drawings:
1 light source, 2 optical switch element, 21 light shielding part, 211 first substrate, 212 second substrate, 213 liquid crystal layer, 214 first polarizer, 215 second polarizer, 216 pixel array substrate, 217 photorefractive crystal, 218 first electrode structure, 219 second electrode structure, 22 control circuit, 3 image recognition module, 31 first image acquisition module, 311 second camera, 32 image processing module, 33 second image acquisition module, 331 first camera, 332 first optical filter, 4 area to be treated or target area, 5 irradiation area, 6 healthy area, 7 beam expansion and collimation mechanism, and s central light path.

DETAILED DESCRIPTION

In order to at least partly solve or alleviate the problem in the related art that when the human skin is irradiated directly by the ultraviolet light source, when the irradiation area of the ultraviolet light source on the human skin exceeds an area to be treated on the human skin, human skin in a healthy area may be damaged, and when the irradiation area of the ultraviolet light source on the human skin cannot cover the area to be treated on the human skin, a part of the area to be treated which is not irradiated by the ultraviolet light cannot be effectively treated, which results in a poor therapeutic effect, the embodiments of the present disclosure provide an irradiation device and a method for using the same. According to some embodiments of the present disclosure, there is provided an irradiation device, comprising: a body of the irradiation device, a light source located on the body of the irradiation device, an optical switch element and an image recognition module communicatively connected to the optical switch element, wherein the image recognition module is configured to recognize a contour of an area to be treated and provide the contour of the area to be treated to the optical switch element, and the optical switch element controls a contour of an irradiation area formed by irradiation of the light source on the area to be treated to match with the contour of the area to be treated provided by the image recognition module. According to some other embodiments of the present disclosure, there is provided a method for using an irradiation device, comprising steps of: recognizing, by an image recognition module, a contour of an area to be treated and providing the contour of the area to be treated to an optical switch element; and controlling, by the optical switch element, a contour of an irradiation area formed by irradiation of the light source on the area to be treated to match with the contour of the area to be treated.

According to some embodiments of the present disclosure, a contour of an area to be treated is recognized by an image recognition module and is provided by the image recognition module to an optical switch element, and a contour of an irradiation area formed by irradiation of a light source on the area to be treated is controlled by the optical switch element according to the contour of the area to be treated provided by the image recognition module to match with the contour of the area to be treated, so that when skin diseases are treated using the irradiation device according to the present disclosure, the contour of the irradiation area of the light source on the area to be treated coincides with the contour of the area to be treated, thereby ensuring a therapeutic effect with respect to the area to be treated while avoiding damages to skin in a healthy area.

In order to make at least some purposes, technical solutions, and advantages of the present disclosure more clear, implementations of some embodiments of the present disclosure will be further described in detail below with reference to the accompanying drawings.

In addition, although the following embodiments all relate to the medical field, the present disclosure is not limited thereto. In fact, some other embodiments of the present disclosure are also applicable to other application scenarios in which a shape, a size, and intensity of an irradiation area need to be adjusted. For example, a shape, a size, a color, intensity, etc. of an irradiation area of visible light from stage lighting during stage performances may need to be adjusted, so as to adjust the lighting effect in real time. As another example, a shape, a size, intensity etc. of an irradiation area of an infrared auxiliary light source of a night-vision instrument carried by a combatant may need to be adjusted during secret military actions at night or in a dark room, so as to achieve night vision while avoiding discovery by others or waking a sleeping wolf etc.

As shown in FIG. 1, the embodiments of the present disclosure provide an irradiation device, comprising a body of the irradiation device (not shown in the figure), a light source 1 located on the body of the irradiation device, an optical switch element 2, and an image recognition module 3 communicatively connected to the optical switch element 2.

The image recognition module 3 is configured to recognize a contour of an area to be treated 4 (or more generally, a target area) on an object (for example, a human body) to be treated and provide the contour of the area to be treated to the optical switch element 2, and the optical switch element 2 controls the light source 1, so that a contour of an irradiation area of the light source 1 matches with the contour of the area to be treated 4.

Figure 2:
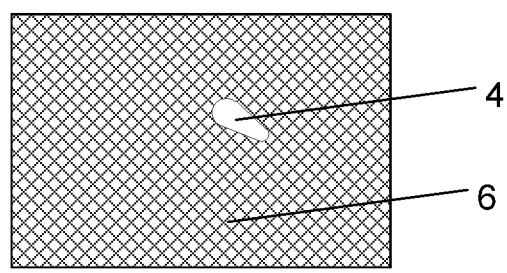
FIG. 2 is a diagram of a scenario in which an area to be treated is included according to another embodiment of the present disclosure.
Figure 3:
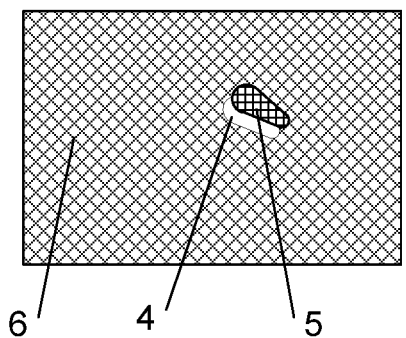
FIG. 3 is a diagram of a scenario in which an area to be treated and an irradiation area are included according to another embodiment of the present disclosure.

As shown in FIG. 2, illustrated is a diagram of a scenario in which an area to be treated 4 is included. For example, when there are pathological changes on human skin, there is an area to be treated 4 in a healthy area 6. As shown in FIG. 3, there is a diagram of a scenario in which an area to be treated 4 and an irradiation area 5 are included, that is, an irradiation area 5 and an area to be treated 4 surrounded by a healthy area 6 during treatment using the irradiation device according to the embodiments of the present disclosure.

When the irradiation device according to the embodiments of the present disclosure is used, a contour of the area to be treated 4 may be firstly recognized by the image recognition module 3 and may be provided by the image recognition module 3 to the optical switch element 2. A contour of the irradiation area 5 of the light source 1 is controlled by the optical switch element 2 according to the contour of the area to be treated 4 provided by the image recognition module 3, so that the contour of the irradiation area 5 matches with the contour of the area to be treated 4. The matching of the contour of the irradiation area 5 with the contour of the area to be treated 4 means that both a shape and a size of the contour of the irradiation area 5 are the same as a shape and a size of the contour of the area to be treated 4, or the shape of the contour of the irradiation area 5 is similar to the shape of the contour of the area to be treated 4 and the size of the contour of the irradiation area 5 is the same as the size of the contour of the area to be treated 4, and during treatment, the irradiation area 5 coincides with the area to be treated 4.

In some embodiments of the present disclosure, the light source 1, the optical switch element 2 and the image recognition module 3 communicatively connected to the optical switch element 2 may be disposed on the body of the irradiation device respectively, and may be directly put into use after being assembled by a manufacturer. In some embodiments, the light source 1 may be configured to emit light within a preset band, such as ultraviolet light, infrared light, or visible light, and the band of the light may be selected according to requirements of different symptoms. For example, when the irradiation device according to the embodiments of the present disclosure is used to treat skin diseases, ultraviolet light having a wavelength between 200 nanometers and 400 nanometers may be emitted by the light source 1. In addition, in some other embodiments of the present disclosure, the light source 1, the optical switch element 2, and the image recognition module 3 communicatively connected to the optical switch element 2 may also be provided in whole or individually, have, for example, a standardized module interface, and may be put into use after being simply assembled by a user (for example, a doctor, a nurse, etc.)

In some embodiments of the present disclosure, the contour of the area to be treated 4 is recognized by the image recognition module 3 and is provided by the image recognition module 3 to the optical switch element 2. The optical switch element 2 controls the contour of the irradiation area 5 of the light source 1 to match with the contour of the area to be treated 4 according to the contour of the area to be treated 4 provided by the image recognition module 3, so that when skin diseases are treated using the irradiation device according to some embodiments of the present disclosure, the contour of the irradiation area 5 of the light source 1 coincides with the contour of the area to be treated 4, thereby ensuring a therapeutic effect with respect to the area to be treated 4 while avoiding damages to skin in the healthy area 6.

Figure 4:
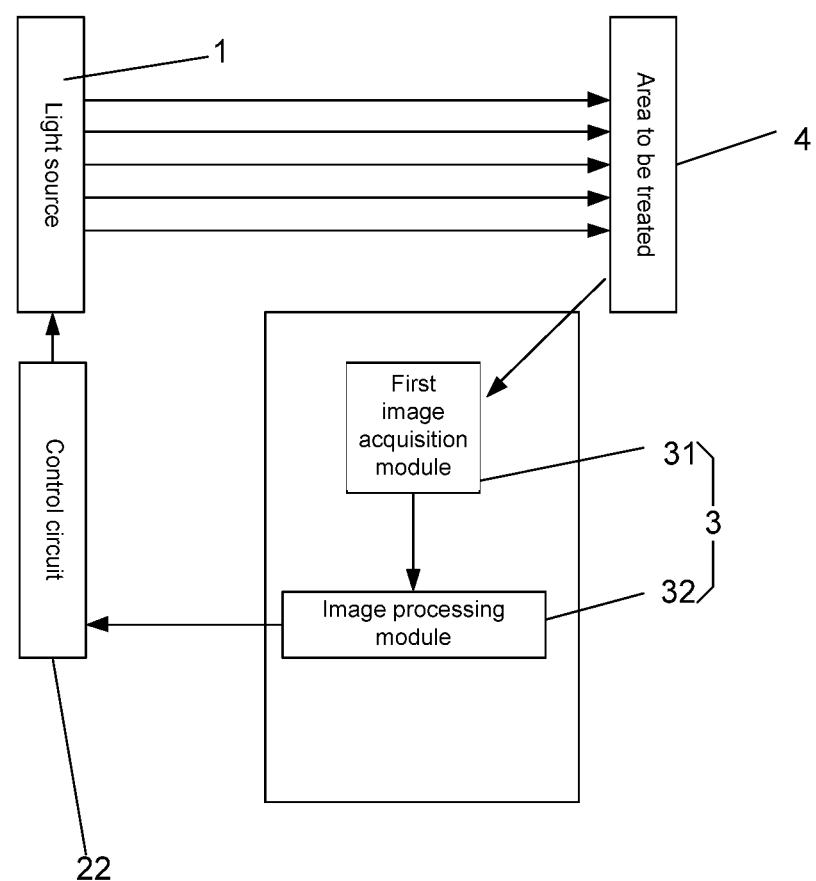
FIG. 4 is a structural diagram of an irradiation device according to another embodiment of the present disclosure.

As shown in FIG. 4, in some embodiments of the present disclosure, when the light source 1 is composed of an array of light emitting points, the optical switch element 2 comprises a control circuit 22, which is connected to the light source 1 and the image recognition module 3 respectively and is configured to control the array of light emitting points in the light source 1 according to the contour of the area to be treated 4, so that a contour of an area formed by array of light emitting points in a turn-on state matches with the contour of the area to be treated 4.

In some embodiments of the present disclosure, the light source control circuit 22 is communicatively connected to the image recognition module 3. The light source control circuit 22 controls the light emitting points in the array of light emitting points of the light source 1 to be turned on or turned off according to the contour of the area to be treated 4 provided by the image recognition module 3, so that the contour of the area formed by the array of light emitting points in a turn-on state matches with the contour of the area to be treated 4 to ensure that the irradiation area 5 of the light source 1 coincides with the area to be treated 4 during treatment, thereby ensuring the therapeutic effect with respect to the area to be treated 4 while avoiding damages to the skin in the healthy area 6.

As shown in FIG. 1, in some embodiments of the present disclosure, when the light source 1 is an ordinary light source 1 or a combination of an ordinary normal light source 1 and a light guide plate, the optical switch element 2 may comprise a control circuit 22 and a light shielding part 21.

The control circuit 22 is connected to the image recognition module 3 and the light shielding part 21, respectively. The control circuit 22 is configured to control the light shielding part 21 to partly shield the light emitted by the light source 1 according to the contour of the area to be treated 4, so that the contour of the irradiation area 5 formed by a part of the light emitted by the light source 1 which is not shielded by the light shielding part 21 matches with the contour of the area to be treated 4.

In some embodiments of the present disclosure, the light shielding part 21 is disposed between the light source 1 and the area to be treated 4. The control circuit 22 controls the light shielding part 21 to partly shield the light emitted by the light source 1 according to the contour of the area to be treated 4, so that the contour of the irradiation area 5 formed by a part of the light emitted by the light source 1 which is not shielded by the light shielding part 21 matches with the contour of the area to be treated 4. The light shielding part 21 is provided flexibly.

In some embodiments, the light source 1 may emit parallel light, and the light shielding part 21 may be in a plate shape and may be disposed in a direction perpendicular to a light path of the light source 1. The light shielding part 21 may have a maximum light shielding area which is the same as a maximum light emitting surface of the light source 1, and have a reasonable structure.

In some embodiments, the light shielding part 21 may be a liquid crystal display panel, and the control circuit 22 may be a liquid crystal display control circuit.

The liquid crystal display control circuit may be configured to control a part of an area of the liquid crystal display panel to be displayed transparently and other parts of the area to be displayed in black according to the contour of the area to be treated 4, and the transparently displayed area matches with the area to be treated 4.

Figure 5:
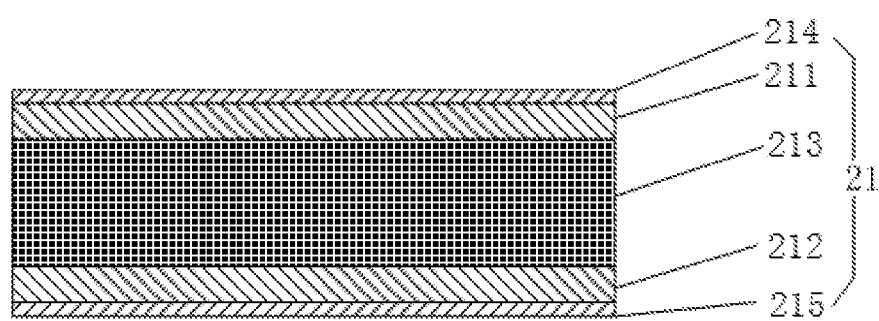
FIG. 5 is a structural diagram of a light shielding part according to another embodiment of the present disclosure.

As shown in FIG. 5, in some embodiments of the present disclosure, the liquid crystal display panel may comprise a first substrate 211, a second substrate 212, a liquid crystal layer 213, a first electrode, and a second electrode. The liquid crystal layer may be disposed between the first substrate 211 and the second substrate 212. The first electrode may be disposed on the first substrate 211, the second electrode may be disposed on the second substrate 212, and the first electrode and the second electrode may be electrically connected to the liquid crystal display control circuit, respectively. The liquid crystal display control circuit may be configured to apply a voltage to the liquid crystal layer 213 through the first electrode and the second electrode according to the contour of the area to be treated 4, so that a part of the light from the light source 1 is transmitted through the liquid crystal layer 213, thereby forming the irradiation area 5 which has a contour of matching with the contour of the area to be treated 4.

In some embodiments of the present disclosure, the first electrode and the second electrode may be conductive patterns formed on the first substrate 211 and the second substrate 212, which correspond to sub-pixels formed by liquid crystals. The liquid crystal display control circuit controls voltages on the first electrode and the second electrode to control a deflection angle of liquid crystal molecules, so as to control a range of the transparently displayed area on the liquid crystal display panel.

In some embodiments of the present disclosure, an image including the area to be treated 4 may be divided into a*b small squares, wherein a is a row number of the small squares, b is a column number of the small squares, and each of the small squares may have a side length of 1 micron. The liquid crystal display panel may comprise a*b sub-pixels, and each of the sub-pixels corresponds to a small square. The liquid crystal display control circuit controls sub-pixels at corresponding positions of the liquid crystal display panel to transmit light or shield light according to the contour of the area to be treated 4, so that the irradiation area 5 formed by the light which is transmitted through the liquid crystal display panel coincides with the area to be treated 4.

Further, it can be understood by those skilled in the art that since degrees of treatment required at different positions within the same area to be treated 4 may be different, that is, intensity of irradiation which is required may be different, in order to ensure the therapeutic effect, different voltages may be applied to different first electrodes and second electrodes to obtain different deflection angles of different liquid crystal molecules, so that different amounts of light may be transmitted through different sub-pixels, thereby controlling the intensity of irradiation and ensuring that the therapeutic effect is achieved according to the embodiments of the present disclosure.

In some embodiments of the present disclosure, the first substrate 211 may be an array substrate and the second substrate 212 may be an opposite substrate, or the first substrate 211 may be an opposite substrate and the second substrate 212 may be an array substrate.

The first electrode may be a pixel electrode and the second electrode may be a common electrode, or the first electrode may be a common electrode and the second electrode may be a pixel electrode.

Types of the first substrate 211, the second substrate 212, the first electrode and the second electrode are not specifically limited, and the effect according to the present disclosure can be achieved as long as the liquid crystal layer is disposed between the first substrate 211 and the second substrate 212 and the first electrode and the second electrode are disposed on the first substrate 211 and the second substrate 212, respectively.

As shown in FIG. 5, the liquid crystal display panel may further comprise a first polarizer 214 and a second polarizer 215. The first polarizer 214 and the second polarizer 215 may be disposed outside the first substrate 211 and the second substrate 212, respectively. In some embodiments, the first polarizer 214 and the second polarizer 215 may be disposed so that optical axes thereof are perpendicular to each other. In this case, the first polarizer 214 may be configured to convert light from the light source 1 into polarized light, and then a polarization direction of the polarized light is deflected by the liquid crystals in a case that the liquid crystals are not powered on, so that the polarized light which is transmitted through the liquid crystal layer 213 may be transmitted through the second polarizer 215, thereby forming a light transmission effect. When the liquid crystal layer 213 is powered on, optical rotation properties of the liquid crystal molecules in the liquid crystal layer 213 disappear, so that the polarization direction of the polarized light is not deflected, and the polarized light cannot be transmitted through the second polarizer 215, thereby forming a light shielding effect. In some other embodiments, the first polarizer 214 and the second polarizer 215 may be disposed so that the optical axes thereof are parallel to each other. In this case, the first polarizer 214 may be configured to convert the light from the light source 1 into polarized light, and then the polarization direction of the polarized light is deflected by the liquid crystals in a case that the liquid crystals are not powered on, so that the polarized light which is transmitted through the liquid crystal layer 213 cannot be transmitted through the second polarizer 215, thereby forming a light shielding effect. When the liquid crystal layer 213 is powered on, the optical rotation properties of the liquid crystal molecules in the liquid crystal layer 213 disappear, so that the polarization direction of the polarized light is not deflected, and the polarized light may be transmitted through the second polarize 215, thereby forming a light transmission effect. Irrespective of how to dispose the first polarizer 214, the liquid crystal layer 213 and the second polarizer 215, it is convenient to control the intensity of irradiation at various positions in the irradiation area 5 formed by the light source 1.

In some embodiments of the present disclosure, the liquid crystal display control circuit is communicatively connected to the image recognition module 3, and the liquid crystal display control circuit controls a pixel region in the liquid crystal display panel according to the contour of the area to be treated 4 provided by the image recognition module 3, so that a part of an area of the liquid crystal display panel is displayed transparently, and other parts of the area of the liquid crystal display panel are displayed in black. Light may be transmitted through the transparently displayed area which matches with an area within the contour of the area to be treated 4, and light is shielded by the black display area. The light emitted by the light source 1 is irradiated on the liquid crystal display panel. A part of the light is transmitted through the transparently displayed area, thereby forming the irradiation area 5, which has a contour matching with the contour of the area to be treated 4, and other parts of the light are absorbed or reflected by the black display area, which avoids damages to the skin in the healthy area 6 due to irradiation from the light source 1 on the basis of ensuring that the therapeutic effect is achieved according to the present disclosure.

Figure 6:
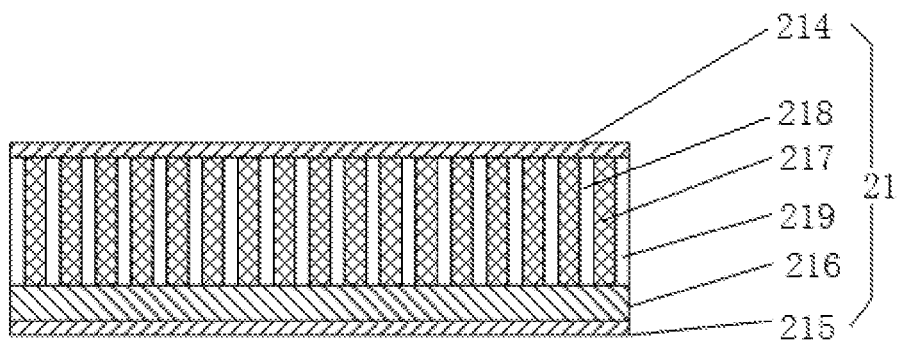
FIG. 6 is a structural diagram of a light shielding part according to another embodiment of the present disclosure.

As shown in FIG. 6, in some other embodiments of the present disclosure, the light shielding part 21 may also be a display panel, which may comprise a pixel array substrate 216 and a photorefractive crystal layer.

The photorefractive crystal layer may be disposed on the pixel array substrate 216, and is located on a side facing the area to be treated 4. The photorefractive crystal layer comprises a plurality of photorefractive crystals 217, which are disposed at equal intervals in a gate line scan direction or a data line scan direction of the display panel. Further, a first electrode structure 218 and a second electrode structure 219 may be disposed outside two opposite sides of each photorefractive crystal 217 respectively, and the first electrode structure 218 and the second electrode structure 219 may be electrically connected to the control circuit 22 respectively. The control circuit 22 may apply a voltage to the photorefractive crystal layer through the first electrode structure 218 and the second electrode structure 219 according to the contour of the area to be treated 4, so that a part of the light from the light source 1 is transmitted through the photorefractive crystal layer, thereby forming the irradiation area 5. Of course, it can be understood by those skilled in the art that there may be a common electrode structure between two adjacent photorefractive crystals 217. The photorefractive crystal 217 may comprise barium titanate, potassium niobate, lithium niobate, bismuth silicate, etc.

As shown in FIG. 6, the display panel may further comprise a first polarizer 214 and a second polarizer 215, which may be disposed outside the pixel array substrate 216 and the photorefractive crystal layer, respectively. In some embodiments, the first polarizer 214 and the second polarizer 215 may be disposed so that optical axes thereof are perpendicular to each other. In this case, the first polarizer 214 and the second polarizer 215 may be configured to convert light from the light source 1 into polarized light, so that the light may be transmitted through the liquid crystal display panel and are then transmitted in a specific direction, for convenience of control of intensity of irradiation at various positions within the irradiation area 5 formed by the light source 1.

As shown in FIG. 1, in some embodiments of the present disclosure, the irradiation device may further comprise a beam expansion and collimation mechanism 7, which may be disposed between the light source 1 and the light shielding part 21, and may be configured to convert linear light emitted by the light source 1 into surface light, so that the light within the irradiation area 5 which is formed by irradiation of the light source 1 on the area to be treated 4 is uniform.

As shown in FIG. 1, in some embodiments of the present disclosure, the image recognition module 3 may comprise a first image acquisition module 31 and an image processing module 32. The first image acquisition module 31 may be configured to acquire a first image including the area to be treated 4.

The image processing module 32 may be configured to recognize the area to be treated 4 from the first image and determine a contour of the area to be treated 4.

In some embodiments of the present disclosure, the image processing module 32 is communicatively connected to the first image acquisition module 31, and may be communicatively connected to the optical switch element 2, and the first image including the area to be treated 4 (as shown in FIG. 2) is acquired by the first image acquisition module 31. In some embodiments, the image processing module 32 may receive the first image, extract features from the image, and perform a contrast enhancement process on an image of the area to be treated 4, so that a boundary between the area to be treated 4 and the healthy area 6 is more obvious. Then, the image processing module 32 may extract a boundary and chroma etc. of the area to be treated 4 as features, determine the contour of the area to be treated 4, convert an image signal into a digital signal and provide the digital signal to the optical switch element 2. In some embodiments, the optical switch element 2 may control the light source 1 according to the contour of the area to be treated 4, so that the contour of the irradiation area 5 matches with the contour of the area to be treated 4, thereby ensuring the therapeutic effect with respect to the area to be treated 4 while avoiding damages to the skin in the healthy area 6.

In some embodiments of the present disclosure, the first image acquisition module 31 may be located on a central light path s of the light source 1, and the first image acquisition module 31 may be located away from the central light path s of the light source 1 when light is emitted by the light source 1.

Figure 7:
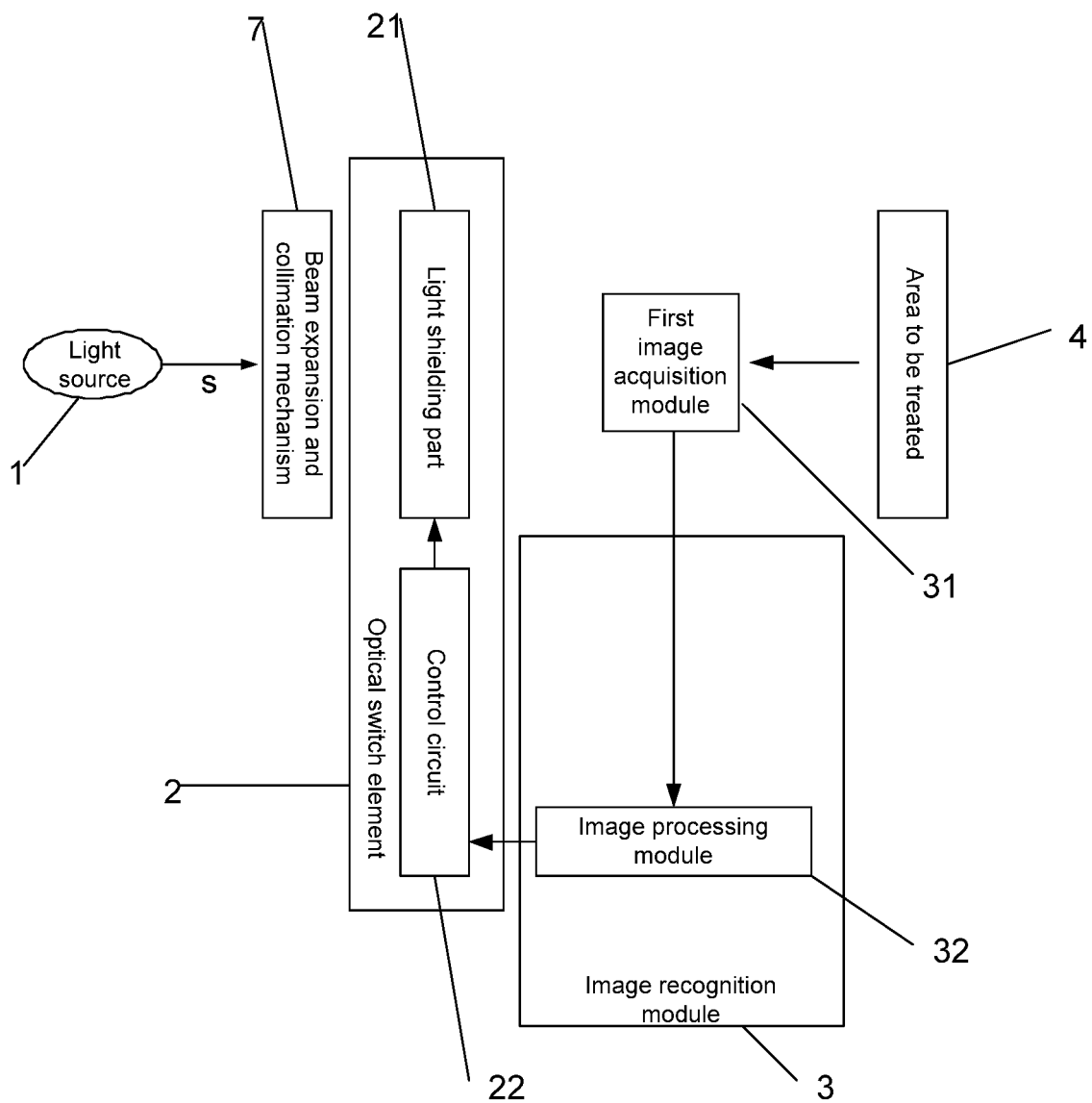
FIG. 7 is a structural diagram of a scenario in which a first image acquisition module is located on a central light path of a light source according to another embodiment of the present disclosure.

As shown in FIG. 7, in some embodiments of the present disclosure, a center of the area to be treated 4 is located on the central light path s of the light source 1. In order to ensure that the obtained first image will not be distorted due to problems such as an angle etc. when the first image acquisition module 31 acquires the first image including the area to be treated 4, the first image acquisition module 31 may be located on the central light path s of the light source 1, that is, the first image acquisition module 31 acquires the first image right in front of the area to be treated 4. When the light source 1 emits light, the first image acquisition module 31 may be located away from the central light path s of the light source 1 to prevent the first image acquisition module 31 from affecting the contour of the irradiation area 5 formed by the light source 1. The image processing module 32 does not need to perform a depth calculation when it recognizes the area to be treated 4 from the first image and determines the contour of the area to be treated 4, which reduces the difficulty in developing the image processing module 32, thereby reducing the development cost of the irradiation device according to some embodiments of the present disclosure.

During the treatment of the diseases by using the irradiation device according to some embodiments of the present disclosure, it is difficult to ensure that a patient does not move as the patient may be very tired to maintain a posture for a long time, and it is also difficult to ensure that the irradiation device according to the embodiments of the present disclosure does not jitter during the use of the irradiation device. As a result, a situation of misalignment between an irradiation area 5 and an area to be treated 4 often occurs (as shown in FIG. 3). In this case, it needs to adjust a position of the irradiation area 5 or a position of the area to be treated 4, to ensure that the area to be treated 4 matches with the irradiation area 5. In the embodiments of the present disclosure, as the position of the irradiation area 5 may be adjusted more precisely than the position of the area to be treated 4, when there is a relative movement between the area to be treated 4 and the irradiation area 5, the position of the irradiation area 5 may be adjusted.

In some embodiments of the present disclosure, the light source 1 may be a light source 1 with an adjustable light emitting wavelength, and emit visible light for a first time period and emit ultraviolet light for a second time period. The first image acquisition module 31 may be configured to collect a second image including the irradiation area 5 and the area to be treated 4 in the first time period. The image processing module 32 may be configured to recognize the irradiation area 5 and the area to be treated 4 from the second image, determine a contour of the irradiation area 5 and a contour of the area to be treated 4 respectively, and compare a position of the contour of the area to be treated 4 with a position of the contour of the irradiation area 5 to determine whether they correspond to each other, and if not, adjust the optical switch element 2 to control the position of the irradiation area 5 of the light source 1 according to the position of the contour of the area to be treated 4 and the position of the contour of the irradiation area 5, so that the contour of the irradiation area 5 matches with the contour of the area to be treated 4.

In some embodiments of the present disclosure, when the light required for treatment is invisible light, such as ultraviolet light or infrared light, the light source 1 may emit visible light without moving the light source 1 and the area to be treated 4. The first image acquisition module 31 acquires the second image including the irradiation area 5 formed by the light source 1 and the area to be treated 4, then determines a contour of the irradiation area 5 and a contour of the area to be treated 4 respectively and provide the contour of the irradiation area 5 and the contour of the area to be treated 4 to the image processing module 32. The image processing module 32 may compare a position of the contour of the area to be treated 4 with a position of the contour of the irradiation area 5 to determine whether they correspond to each other, and if not, adjust the optical switch element 2 to control the position of the irradiation area 5 of the light source 1 according to the position of the contour of the area to be treated 4 and the position of the contour of the irradiation area 5, so that the contour of the irradiation area 5 matches with the contour of the area to be treated 4. When the contour of the irradiation area 5 coincides with the contour of the area to be treated 4, the process proceeds to the second time period, in which the light source 1 emits invisible light to treat a patient and the irradiation area 5 is intermittently adjusted, so that the irradiation area 5 always matches with the area to be treated 4.

When the light required for treatment is visible light, the first image acquisition module 31 may directly acquire a second image including the irradiation area 5 of the light source 1 and the area to be treated 4 in time, then determine a contour of the irradiation area 5 and a contour of the area to be treated 4 respectively, and provide the contour of the irradiation area 5 and the contour of the area to be treated 4 to the image processing module 32. The image processing module 32 compares a position of the contour of the area to be treated 4 with a position of the contour of the irradiation area 5 to determine whether they correspond to each other, and if not, adjust the optical switch element 2 to control the position of the irradiation area 5 of the light source 1 according to the position of the contour of the area to be treated 4 and the position of the contour of the irradiation area 5, so that the contour of the irradiation area 5 matches with the contour of the area to be treated 4.

In some embodiments of the present disclosure, adjusting the position of the irradiation area 5 of the light source 1 may specifically comprise: calculating a distance between a central point of the irradiation area 5 and a central point of the area to be treated 4 by comparing distances between five consecutive points on the contour of the irradiation area 5 with five points at corresponding positions on the contour of the area to be treated 4, obtaining an adjustment amount required for adjusting the position of the irradiation area 5, and adjusting the position of the irradiation area 5 according to the adjustment amount. However, the present disclosure is not limited to five points, and any other number of points may also be feasible.

Figure 9:
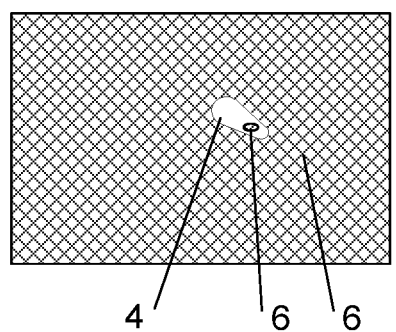
FIG. 9 is a diagram of a scenario in which an area to be treated is included when a part of the area to be treated is recovered before other parts of the area to be treated according to another embodiment of the present disclosure.

Of course, there may also be a situation in which a part of the area to be treated 4 is recovered before other parts of the area to be treated 4 during the treatment. As shown in FIG. 9, illustrated is a diagram of positions of the area to be treated 4 and the healthy area 6 when a part of the area to be treated 4 is recovered before other parts of the area to be treated 4. In this case, the contour of the area to be treated 4 changes, and correspondingly, it needs to adjust the contour of the irradiation area 5. Thereby, the image processing module 32 re-controls the contour of the irradiation area 5 to match with the contour of the area to be treated 4 according to the contour of the area to be treated 4 and the contour of the irradiation area 5 determined from the second image, so as to ensure that the irradiation area 5 of the light source 1 always coincides with the area to be treated 4.

In some embodiments of the present disclosure, the optical switch element 2 needs to re-control the contour of the irradiation area 5 to match with the contour of the area to be treated 4 in the following cases.

In a first case, the optical switch element 2 only needs to control a shape of the contour of the irradiation area 5 to match with a shape of the contour of the area to be treated 4, which is suitable for a situation in which only a part of the area to be treated 4 is recovered before other parts of the area to be treated 4.

In a second case, the optical switch element 2 only needs to control a position of the contour of the irradiation area 5 to match with a position of the contour of the area to be treated 4, which is suitable for a situation in which only a relative movement between the contour of the area to be treated 4 and the contour of the irradiation area 5 occurs.

In a third case, the optical switch element 2 needs to control both the shape and the position of the contour of the irradiation area 5 to match with the shape and the position of the contour of the area to be treated 4, which is suitable for a situation in which a relative movement between the area to be treated 4 and the irradiation area 5 occurs and a part of the area to be treated 4 is recovered before other parts of the area to be treated 4.

Figure 8:
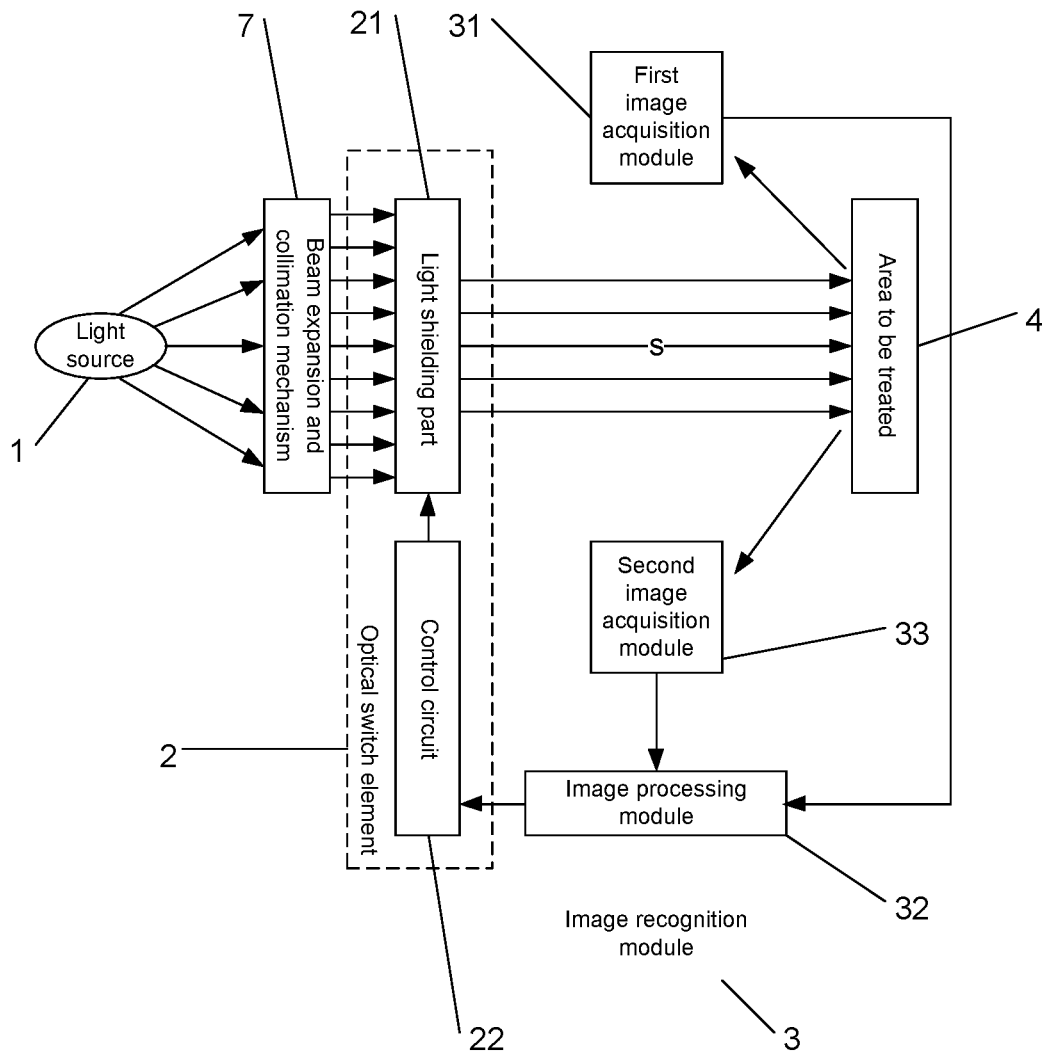
FIG. 8 is a structural diagram of an irradiation device according to another embodiment of the present disclosure.

As shown in FIG. 8, in some embodiments of the present disclosure, when the light required for treatment is invisible light, such as ultraviolet light or infrared light, in order to adjust the irradiation area 5 in time, a second image acquisition module 33 is configured to acquire a third image including the irradiation area 5; and the first image acquisition module 31 is further configured to acquire a fourth image currently including the area to be treated 4.

The image processing module 32 is configured to recognize the irradiation area 5 from the third image, determine a contour of the irradiation area 5, recognize the area to be treated 4 from the fourth image, determine a contour of the area to be treated 4, and compare the contour of the area to be treated 4 with the contour of the irradiation area 5 to determine whether they correspond to each other, and if not, adjust the optical switch element 2 to control the contour of the irradiation area 5 to match with the contour of the area to be treated 4 according to the contour of the area to be treated 4 and the contour of the irradiation area 5.

In some embodiments of the present disclosure, the second image acquisition module 33 acquires the third image including the irradiation area 5, and the first image acquisition module 31 acquires the fourth image currently including the area to be treated 4. The image processing module 32 recognizes the irradiation area 5 from the third image, determines a contour of the irradiation area 5, recognizes the area to be treated 4 from the fourth image, determines a current contour of the area to be treated 4, and then compare the contour of the irradiation area 5 with the contour of the area to be treated 4 to determine whether they correspond to each other, and if not, adjust the optical switch element 2 to control the contour of the irradiation area 5 of the light source 1 according to the contour of the area to be treated 4 and the contour of the irradiation area 5, so that the contour of the irradiation area 5 matches with the contour of the area to be treated 4, to achieve real-time adjustment of the irradiation area 5. In some embodiments, the method for comparing the contour of the irradiation area 5 with the contour of the area to be treated 4 to determine whether they correspond to each other and the method for controlling the contour of the irradiation area 5 which is formed by irradiation of the light source 1 on the area to be treated 4 may be as described above.

Figure 10:
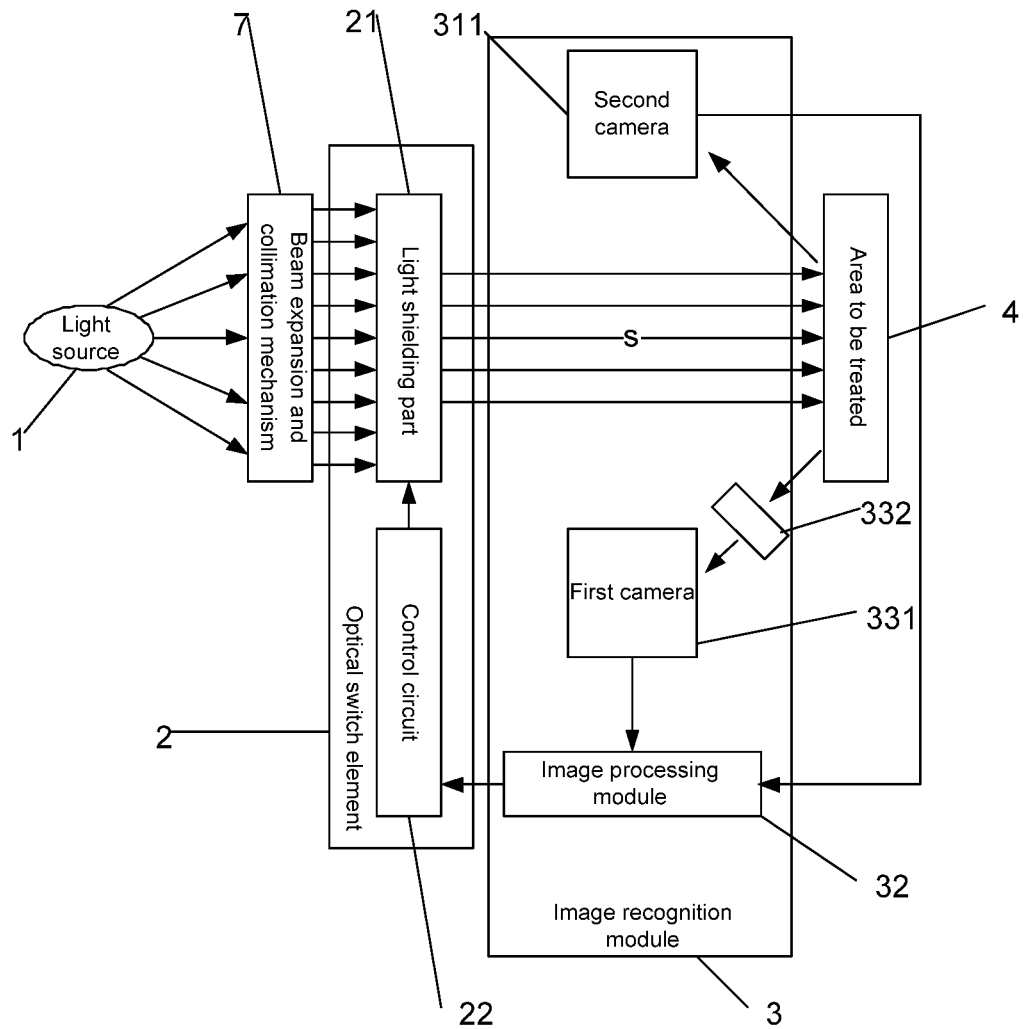
FIG. 10 is a structural diagram of an irradiation device according to another embodiment of the present disclosure.

As shown in FIG. 10, in some embodiments of the present disclosure, the second image acquisition module 33 may comprise a first camera 311 and a first optical filter 332. The first optical filter 332 may be disposed on an external light incident side of the first camera 311. The first camera 311 may be configured to capture the third image through the first optical filter 332.

In the embodiments of the present disclosure, as an ordinary camera cannot capture the contour of the irradiation area 5 formed by irradiation of the invisible light on the area to be treated 4, the first optical filter 332 is disposed on the external light incident side of the first camera 311, so that the first camera 311 captures a third image which comprises only the irradiation area 5 formed by irradiation of the invisible light. In this way, a simple structure is realized and a clear third image is acquired.

As shown in FIG. 10, in some embodiments of the present disclosure, the first image acquisition module 31 may be a second camera 311. The first camera 331 and the second camera 311 may be located on two sides of the central light path s of the light source 1 respectively and have their shooting angles to be mirror symmetrical with respect to the central light path s of the light source 1.

In some embodiments of the present disclosure, the central light path s of the light source 1 refers to one of light paths of the light source 1 which passes through a center of the light source 1 and is perpendicular to the area to be treated 4. The first camera 331 and the second camera 311 may be disposed between the optical switch element 2 and the area to be treated 4. The first camera 331 and the second camera 31 are located on two sides of the central light path s of the light source 1 respectively and have shooting angles which are mirror symmetrical with respect to the central light path s. In this way, in a process that the image processing module 32 compares the contour of the area to be treated 4 with the contour of the irradiation area 5 at the same time to determine whether they correspond to each other, a symmetrization process may be performed on the contour of the irradiation area 5 with respect to the central light path s of the light source 1, and then the processed contour of the irradiation area 5 is compared with the contour of the area to be treated 4 to determine whether they correspond to each other. There is no need to perform a depth calculation during the comparison, which reduces the difficulty in developing the image acquisition module, thereby reducing the development cost of the irradiation device according to some embodiments of the present disclosure.

When the shooting angles of the first camera 331 and the second camera 311 are not mirror symmetrical with respect to the central light path s of the light source 1, the first camera 331 and the second camera 311 may be cameras with a depth calculation function, such as depth cameras. The first camera 331 and the second camera 311 may obtain a relationship between the contour of the area to be treated 4 and the contour of the irradiation area 5 through calculation according to information such as the contour of the area to be treated 4 and the contour of the irradiation area 5, a distance between the first camera 331 and the second camera 311 and distances from the first camera 331 and the second camera 311 to a center of the area to be treated 4 etc., so as to control the contour of the irradiation area 5 to match with the contour of the area to be treated 4.

Figure 11:
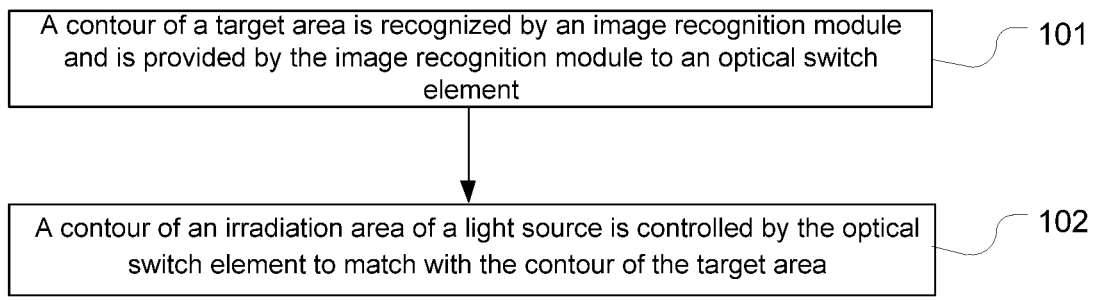
FIG. 11 is a flowchart of a method for using an irradiation device according to another embodiment of the present disclosure.

As shown in FIG. 11, some embodiments of the present disclosure provide a method for using an irradiation device, which may be implemented by the irradiation device as described above. The method may comprise the following steps.

In step 101, a contour of an area to be treated (or more generally, a target area) may be recognized by an image recognition module and may be provided by the image recognition module to an optical switch element.

In some embodiments of the present disclosure, an image recognition module of the irradiation device is communicatively connected to the optical switch element, and may be configured to recognize the contour of the area to be treated and provide the recognized contour of the area to be treated to the optical switch element. The image recognition module may comprise a first image acquisition module and an image processing module. The first image acquisition module may be configured to acquire a first image including the area to be treated. The image processing module may be configured to recognize the area to be treated from the first image, determine the contour of the area to be treated, and provide the contour of the area to be treated to the optical switch element.

In step 102, a contour of an irradiation area of a light source may be controlled by the optical switch element to match with the contour of the area to be treated.

In some embodiments of the present disclosure, the optical switch element may be configured to control the contour of the irradiation area of the light source to match with the contour of the area to be treated according to the contour of the area to be treated.

When the light source is composed of an array of light emitting points, the optical switch element may comprise a light source control circuit, and controls the contour of the irradiation area of the light source to match with the contour of the area to be treated provided by the image recognition module, which comprises: controlling the array of light emitting points in the light source, so that a contour of an area formed by the array of light emitting points in a turn-on state matches with the contour of the area to be treated.

In this case, the light source control circuit may be communicatively connected to the image recognition module, and may be configured to control the light emitting points in the array of light emitting points of the light source to be turned on or turned off according to the contour of the area to be treated provided by the image recognition module, so that the contour of the area formed by the array of light emitting points in a turn-on state matches with the contour of the area to be treated to ensure that the irradiation area of the light source coincides with the area to be treated during the treatment, thereby ensuring the therapeutic effect with respect to the area to be treated while avoiding damages to the skin in the healthy area.

When the light source is an ordinary light source or a combination of a backlight and a light guide plate, the optical switch element may comprise a control circuit and a light shielding part. The control circuit may be communicatively connected to the image recognition module, the light shielding part may be disposed between the light source and the area to be treated, and may be electrically connected to the control circuit. The control circuit may be configured to control the light shielding part to partly shield the light emitted by the light source according to the contour of the area to be treated, so that a contour of an irradiation area formed by a part of the light emitted by the light source which is not shielded by the light shielding part matches with the contour of the area to be treated.

The light shielding part may be a liquid crystal display panel or a display panel. When the light shielding part is a liquid crystal display panel, the contour of the irradiation area of the light source is controlled by the optical switch element to match with the contour of the area to be treated provided by the image recognition module, which comprises: controlling a part of an area of the liquid crystal display panel to be displayed transparently and other parts of the area to be displayed in black, wherein the transparently displayed area corresponds to an area within the contour of the area to be treated.

In some embodiments of the present disclosure, the liquid crystal display panel may comprise: a first substrate, a second substrate, a liquid crystal layer, a first electrode, and a second electrode. The liquid crystal layer is disposed between the first substrate and the second substrate, the first electrode may be disposed on the first substrate, the second electrode may be disposed on the second substrate, and the first electrode and the second electrode may be electrically connected to the liquid crystal display control circuit respectively. The liquid crystal display control circuit may be configured to apply a voltage to the liquid crystal layer through the first electrode and the second electrode according to the contour of the area to be treated, so that a part of light from the light source is transmitted through the liquid crystal layer, thereby forming an irradiation area which has a contour matching with the contour of the area to be treated.

In some embodiments of the present disclosure, the first electrode and the second electrode may be conductive patterns formed on the first substrate and the second substrate, which correspond to sub-pixels formed by liquid crystals. The liquid crystal display control circuit controls voltages on the first electrode and the second electrode to control a deflection angle of liquid crystal molecules, so as to control a range of the transparently displayed area on the liquid crystal display panel.

In the embodiments of the present disclosure, an image including the area to be treated may be divided into a*b small squares, wherein a is a row number of the small squares, b is a column number of the small squares, and each of the small squares may have a side length of 1 micron. The liquid crystal display panel comprises a*b sub-pixels, and each of the sub-pixels corresponds to a small square. The liquid crystal display control circuit may control sub-pixels at corresponding positions of the liquid crystal display panel to transmit light or shield light according to the contour of the area to be treated, so that the irradiation area formed by the light which is transmitted through the liquid crystal display panel coincides with the area to be treated.

In some embodiments of the present disclosure, a contour of an area to be treated is recognized by an image recognition module and is provided by the image recognition module to an optical switch element, and a contour of an irradiation area of the light source is controlled by the optical switch element to match with the contour of the area to be treated provided by the image recognition module according to the contour of the area to be treated, so that when skin diseases are treated using the irradiation device according to some embodiments of the present disclosure, the contour of the irradiation area of the light source coincides with the contour of the area to be treated, thereby ensuring a therapeutic effect with respect to the area to be treated while avoiding damages to the skin in the healthy area.

Figure 12:
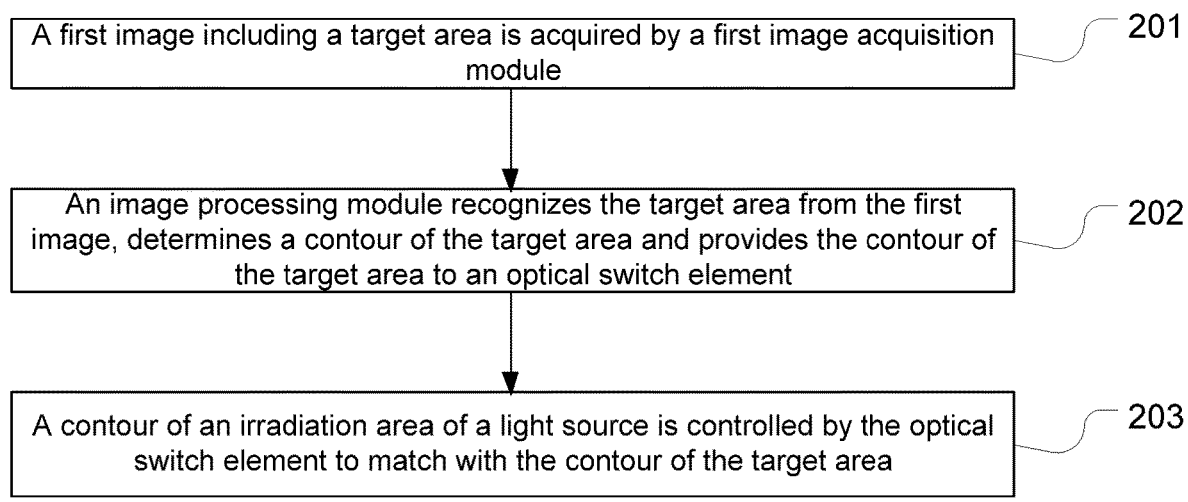
FIG. 12 is a flowchart of a method for using an irradiation device according to another embodiment of the present disclosure.

As shown in FIG. 12, in step 201, a first image including an area to be treated (or more generally, a target area) may be acquired by a first image acquisition module.

In some embodiments of the present disclosure, the first image acquisition module may be a camera, through which the first image including the area to be treated on human skin may be captured.

In step 202, an image processing module may recognize the area to be treated from the first image, determine a contour of the area to be treated and provide the contour of the area to be treated to an optical switch element.

In some embodiments of the present disclosure, the image processing module may receive the first image including the area to be treated which is acquired by the first acquisition module, then extract features from the image, and perform a contrast enhancement process on an image of the area to be treated, so that a boundary between the area to be treated and the healthy area is more obvious. Then, the image processing module may extract a boundary and chroma etc. of the area to be treated as features, determine the contour of the area to be treated, convert an image signal into a digital signal and provide the digital signal to the optical switch element.

In step 203, a contour of an irradiation area of a light source may be controlled by the optical switch element to match with the contour of the area to be treated.

The optical switch element may receive the digital signal carrying contour information of the area to be treated which is provided by the image processing module, and control the contour of the irradiation area of the light source to match with the contour of the area to be treated.

In some embodiments of the present disclosure, a contour of an area to be treated is recognized by an image recognition module and is provided by the image recognition module to an optical switch element, and a contour of an irradiation area of the light source is controlled by the optical switch element to match with the contour of the area to be treated provided by the image recognition module according to the contour of the area to be treated, so that when skin diseases are treated using the irradiation device according to the present disclosure, the contour of the irradiation area of the light source coincides with the contour of the area to be treated, thereby ensuring a therapeutic effect with respect to the area to be treated while avoiding damages to the skin in the healthy area.

Figure 13:
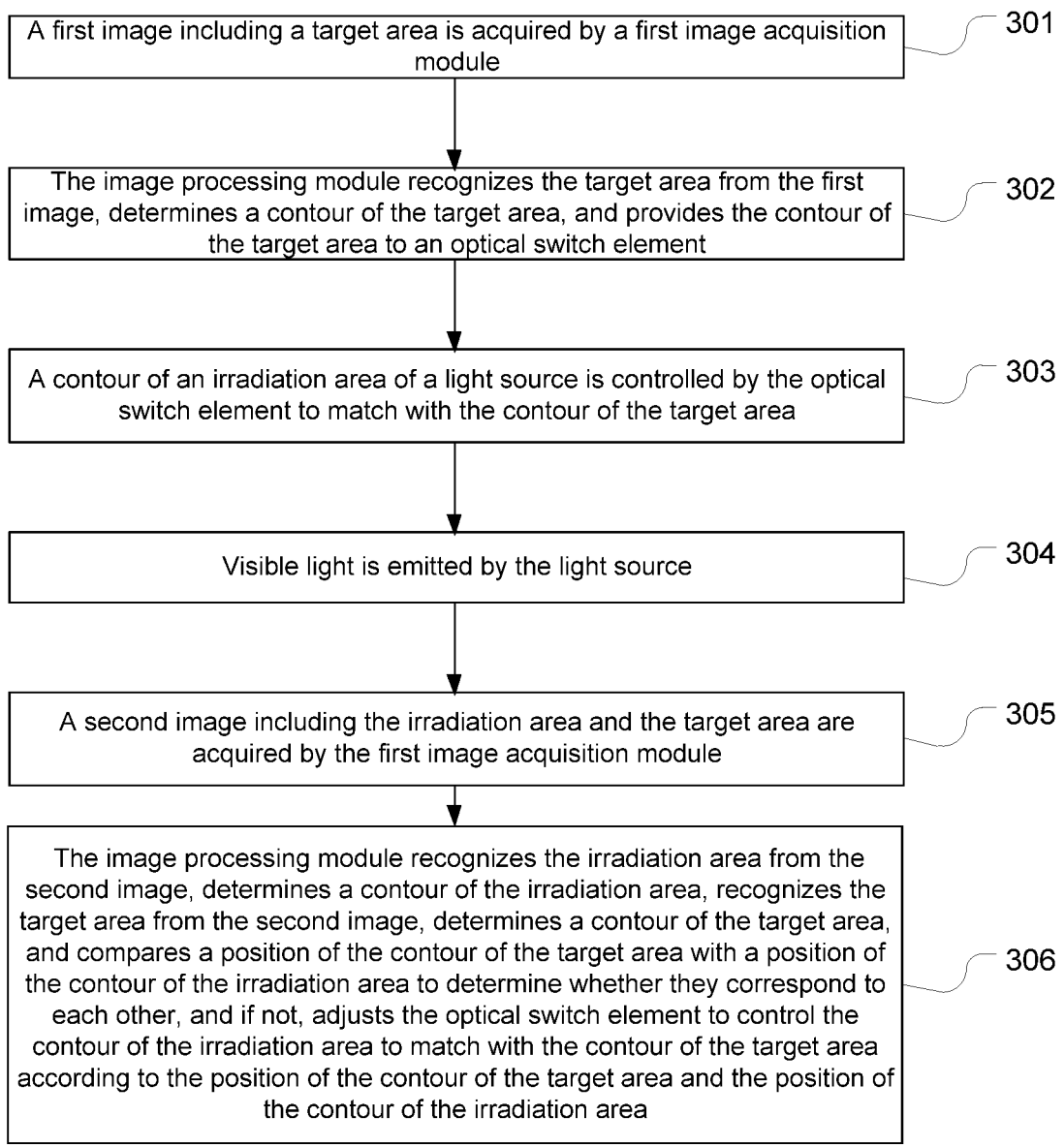
FIG. 13 is a flowchart of a method for using an irradiation device according to another embodiment of the present disclosure.

As shown in FIG. 13, some embodiments of the present disclosure provide a method for using an irradiation device, which may be implemented by the irradiation device described above. The method may comprise the following steps.

In step 301, a first image including an area to be treated (or more generally, a target area) may be acquired by a first image acquisition module.

In some embodiments of the present disclosure, the first image acquisition module may be a camera, through which the first image including the area to be treated on human skin may be captured.

In step 302, the image processing module may recognize the area to be treated from the first image, determine a contour of the area to be treated, and provide the contour of the area to be treated to an optical switch element.

In some embodiments of the present disclosure, the image processing module may receive the first image including the area to be treated which is acquired by the first acquisition module, then extract features from the image, and perform a contrast enhancement process on an image of the area to be treated, so that a boundary between the area to be treated and the healthy area is more obvious. Then, the image processing module may extract a boundary and chroma etc. of the area to be treated as features, determine the contour of the area to be treated, convert an image signal into a digital signal and provide the digital signal to the optical switch element.

In step 303, a contour of an irradiation area of a light source may be controlled by the optical switch element to match with the contour of the area to be treated.

The optical switch element receives the digital signal carrying contour information of the area to be treated which is provided by the image processing module, and controls the contour of the irradiation area of the light source to match with the contour of the area to be treated.

In step 304, visible light may be emitted by the light source.

In some embodiments of the present disclosure, the light source may be a light source with an adjustable light emitting wavelength, and emit visible light for a first time period and emit ultraviolet light for a second time period. When the light source emits visible light, both the irradiation area of the light source and the area to be treated are visible, and images thereof may be captured by the same image acquisition module. Of course, when the light used for treatment is visible light, the light source may only need to emit the visible light.

In step 305, a second image including the irradiation area and the area to be treated may be acquired by the first image acquisition module.

In some embodiments of the present disclosure, the first image acquisition module may be a camera, through which the second image including the irradiation area and the area to be treated on the human skin may be captured. The second image comprises the irradiation area and the area to be treated at a time point, for convenience of intuitive analysis of whether the contour of the irradiation area matches with the contour of the area to be treated.

In step 306, the image processing module may recognize the irradiation area from the second image, determine a contour of the irradiation area, recognize the area to be treated from the second image, determine a contour of the area to be treated, and compare a position of the contour of the area to be treated with a position of the contour of the irradiation area to determine whether they correspond to each other, and if not, adjust the optical switch element to control the contour of the irradiation area to match with the contour of the area to be treated according to the position of the contour of the area to be treated and the position of the contour of the irradiation area.

In some embodiments of the present disclosure, the image processing module may receive the second image including the area to be treated and the irradiation area which is acquired by the first acquisition module, then extract features from the image, and perform a contrast enhancement process on an image of the area to be treated and an image of the irradiation area, so that a boundary between the area to be treated and the healthy area and a boundary between the irradiation area and the healthy area are more obvious. Then, the image processing module may extract a boundary and chroma etc. of the area to be treated and a boundary and chroma etc. of the irradiation area as features, determine a contour of the area to be treated and a contour of the irradiation area, and compare a position of the contour of the irradiation area with a position of the contour of the area to be treated to determine whether they correspond to each other, and if not, adjust the optical switch element to re-control the irradiation area to match with the area to be treated.

In some embodiments of the present disclosure, a contour of an area to be treated is recognized by an image recognition module and is provided by the image recognition module to an optical switch element, and a contour of an irradiation area of the light source is controlled by the optical switch element to match with the contour of the area to be treated provided by the image recognition module according to the contour of the area to be treated, so that when skin diseases are treated using the irradiation device according to the present disclosure, the contour of the irradiation area of the light source coincides with the contour of the area to be treated, thereby ensuring a therapeutic effect with respect to the area to be treated while avoiding damages to the skin in the healthy area.

Figure 14:
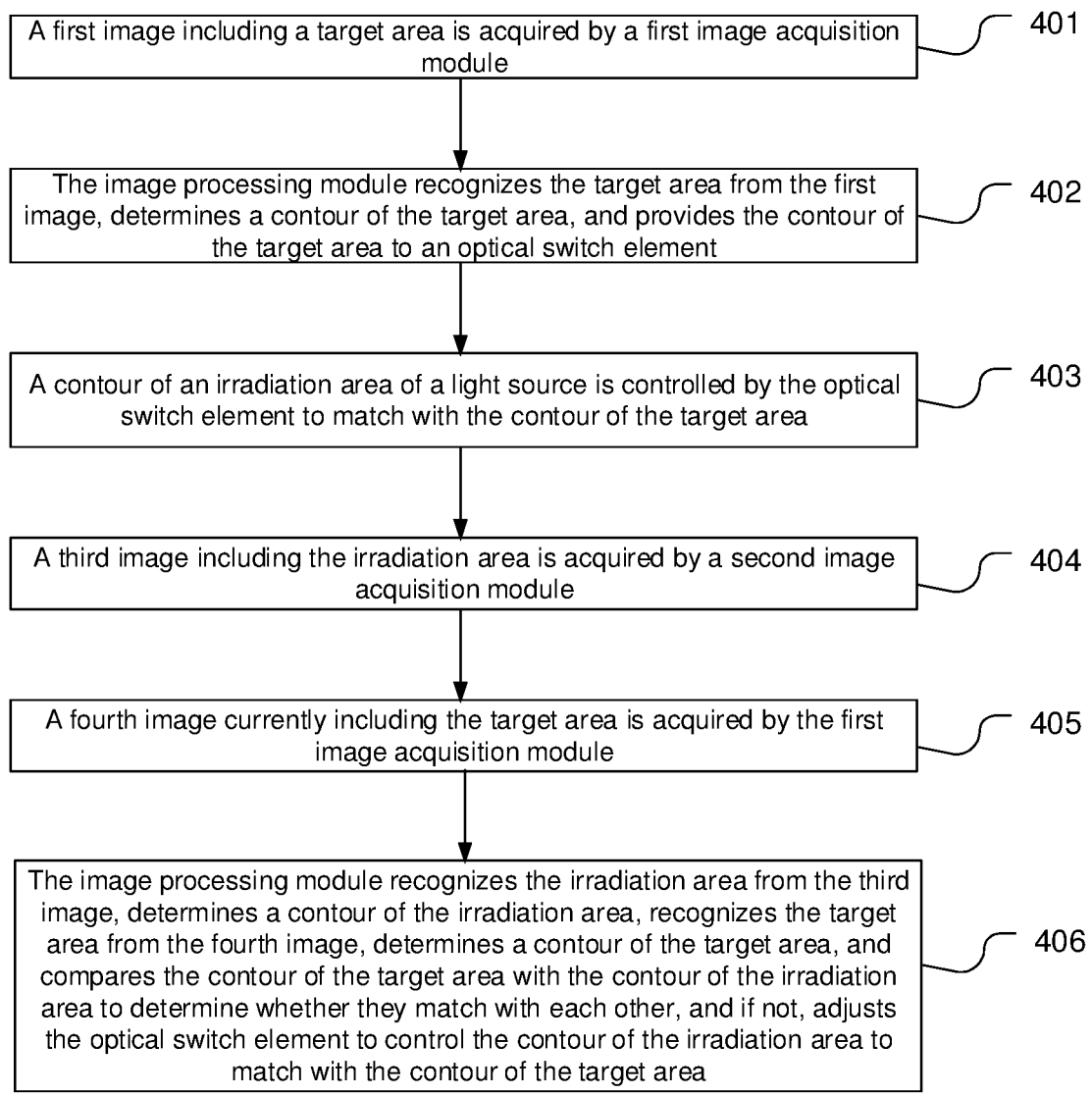
FIG. 14 is a flowchart of a method for using an irradiation device according to another embodiment of the present disclosure.

As shown in FIG. 14, some embodiments of the present disclosure provide a method for using an irradiation device, which may be implemented by the irradiation device described above. The method may comprise the following steps.

In step 401, a first image including an area to be treated (or more generally, a target area) may be acquired by a first image acquisition module.

In some embodiments of the present disclosure, the first image acquisition module may be a camera, through which the first image including the area to be treated on human skin may be captured.

In step 402, the image processing module may recognize the area to be treated from the first image, determine a contour of the area to be treated, and provide the contour of the area to be treated to an optical switch element.

In some embodiments of the present disclosure, the image processing module may receive the first image including the area to be treated which is acquired by the first acquisition module, then extract features from the image, and perform a contrast enhancement process on an image of the area to be treated, so that a boundary between the area to be treated and the healthy area is more obvious. Then, the image processing module may extract a boundary and chroma etc. of the area to be treated as features, determine the contour of the area to be treated, convert an image signal into a digital signal and provide the digital signal to the optical switch element.

In step 403, a contour of an irradiation area of a light source may be controlled by the optical switch element to match with the contour of the area to be treated.

The optical switch element may receive the digital signal carrying contour information of the area to be treated which is provided by the image processing module, and control the contour of the irradiation area of the light source to match with the contour of the area to be treated.

In step 404, a third image including the irradiation area may be acquired by a second image acquisition module.

When the light used for treatment is invisible light, in order to avoid a situation in which the therapeutic effect realized using the irradiation device is poor or skin in a healthy area is damaged due to a relative movement between the irradiation area and the area to be treated or recovery of a part of the area to be treated before other parts of the area to be treated during the treatment, the third image including the irradiation area may be acquired by the second image acquisition module.

As an ordinary camera cannot capture a contour of an irradiation area formed by invisible light, the second image acquisition module may comprise a camera and an optical filter. The optical filter may be disposed on an external light incident side of the first camera. The first camera may be configured to capture the third image through the first optical filter. In this way, a simple structure is realized and a clear third image is acquired.

In step 405, a fourth image currently including the area to be treated may be acquired by the first image acquisition module.

In some embodiments of the present disclosure, when the second image acquisition module acquires the third image including the irradiation area, the fourth image including the area to be treated may be acquired by the first image acquisition module to obtain the contour of the irradiation area and the contour of the area to be treated at the same time.

The second image acquisition module may comprise a first camera and a first optical filter, and the first image acquisition module may comprise a second camera. The first camera and the second camera may be located on two sides of a central light path of the light source respectively and have shooting angles which are mirror symmetrical with respect to the central light path of the light source. In a process that the image processing module compares the contour of the area to be treated with the contour of the irradiation area to determine whether they correspond to each other, a symmetrization process may be firstly performed on the contour of the irradiation area with respect to the central light path of the light source, and then the processed contour of the irradiation area is compared with the contour of the area to be treated to determine whether they correspond to each other. There is no need to perform a depth calculation during the comparison, which reduces the difficulty in developing the image acquisition module, thereby further reducing the development cost of the irradiation device according to some embodiments of the present disclosure.

When the shooting angles of the first camera and the second camera are not mirror symmetrical with respect to the central light path of the light source, the first camera and the second camera may be cameras with a depth calculation function. The first camera and the second camera may obtain information on the contour of the area to be treated and the contour of the irradiation area through calculation according to information such as the contour of the area to be treated and the contour of the irradiation area, a distance between the first camera and the second camera and distances from the first camera and the second camera to a center of the area to be treated etc., and provide a result of the calculation to the image processing module.

In step 406, the image processing module may recognize the irradiation area from the third image, determine a contour of the irradiation area, recognize the area to be treated from the fourth image, determine a contour of the area to be treated, and compare the contour of the area to be treated with the contour of the irradiation area to determine whether they match with each other, and if not, adjust the optical switch element to control the contour of the irradiation area to match with the contour of the area to be treated.

The image processing module recognizes the irradiation area from the third image, determines a contour of the irradiation area, recognizes the area to be treated from the fourth image, determines a contour of the area to be treated, and then compares the contour of the area to be treated with the contour of the irradiation area to determine whether they match with each other, and if not, adjusts the optical switch element to control the contour of the irradiation area to match with the contour of the area to be treated, to ensure that the irradiation area always coincides with the area to be treated, thereby ensuring that a therapeutic effect is achieved according to some embodiments of the present disclosure while avoiding damages to skin in the healthy area.

In some embodiments of the present disclosure, a contour of an area to be treated is recognized by an image recognition module and is provided by the image recognition module to an optical switch element, and a contour of an irradiation area of the light source is controlled by the optical switch element to match with the contour of the area to be treated provided by the image recognition module according to the contour of the area to be treated, so that when skin diseases are treated using the irradiation device according to some embodiments of the present disclosure, the contour of the irradiation area of the light source coincides with the contour of the area to be treated, thereby ensuring a therapeutic effect with respect to the area to be treated while avoiding damages to the skin in the healthy area.

The above description is merely some embodiments of the present disclosure, and is not intended to limit the present disclosure. Any modifications, equivalent substitutions, improvements, etc. made within the spirit and principle of the present disclosure should be included in the protection scope of the present disclosure.

We claim:

1. An irradiation device, comprising:
   a light source, which is a light source with an adjustable light emitting wavelength, configured to emit visible light for a first time period and to emit ultraviolet light for a second time period;
   an optical switch element comprising:
      a light shielding part which is a liquid crystal display panel; and
      a control circuit, which is a liquid crystal display control circuit, communicatively connected to an image recognition module and the light shielding part, respectively, and is configured to control the light shielding part to partly shield light emitted by the light source according to a contour of a target area such that a contour of an irradiation area formed by a part of the light emitted by the light source which is not shielded by the light shielding part matches with the contour of the target area, by controlling a part of an area of the liquid crystal display panel to be displayed transparently and other parts of the area to be displayed in black according to the contour of the target area, wherein the transparently displayed area matches with the target area; and
   an image recognition module communicatively connected to the optical switch element and comprising:
      a first image acquisition module configured to acquire a first image comprising the target area in the second time period and acquire a second image comprising the irradiation area and the target area in the first time period; and
      an image processing module configured to recognize the target area from the first image, determine and recognize the contour of the target area, and provide the contour of the target area to the optical switch element, and further configured to recognize the irradiation area and the target area from the second image, determine the contour of the irradiation area, and compare a position of the contour of the target area with a position of the contour of the irradiation area to determine whether they correspond to each other, and if not, adjust the optical switch element to control the contour of the irradiation area to match with the contour of the target area according to the position of the contour of the target area and the position of the contour of the irradiation area,
   wherein the light source and the target area are located on different sides of the light shielding part.

2. The irradiation device according to claim 1, wherein a maximum light shielding area of the light shielding part corresponds to a maximum light emitting surface of the light source.

3. The irradiation device according to claim 1, wherein the light shielding part is a display panel, which comprises a pixel array substrate and a photorefractive crystal layer.

4. The irradiation device according to claim 1, further comprising: a beam expansion and collimation mechanism disposed between the light source and the light shielding part and configured to convert linear light emitted by the light source into surface light.

5. The irradiation device according to claim 1, wherein the first image acquisition module is located on a central light path of the light source, and the first image acquisition module is located away from an emitting light path of the light source when light is emitted by the light source.

6. The irradiation device according to claim 1, further comprising:
   a second image acquisition module configured to acquire a third image comprising the irradiation area,
   wherein the first image acquisition module is further configured to acquire a fourth image currently comprising the target area; and
   wherein the image processing module is configured to recognize the irradiation area from the third image, determine a contour of the irradiation area, recognize the target area from the fourth image, determine a contour of the target area, compare the contour of the target area with the contour of the irradiation area to determine whether they correspond to each other, and if not, adjust the optical switch element to control the contour of the irradiation area to match with the contour of the target area according to the contour of the target area and the contour of the irradiation area.

7. The irradiation device according to claim 6, wherein the second image acquisition module comprises:
   a first camera; and
   a first optical filter disposed on an external light incident side of the first camera, wherein the first camera is configured to capture the third image through the first optical filter.

8. The irradiation device according to claim 7, wherein the first image acquisition module comprises a second camera, and the first camera and the second camera are located on two sides of a central light path of the light source, respectively, and have their shooting angles to be mirror symmetrical with respect to the central light path of the light source.

9. A method for using the irradiation device according to claim 1, comprising:
   recognizing, by the image recognition module, the contour of the target area and providing the contour of the target area to the optical switch element; and
   controlling, by the optical switch element, the light source, so that the contour of the irradiation area of the light source matches with the contour of the target area.

10. The method according to claim 9, wherein controlling, by the optical switch element, the light source, so that the contour of the irradiation area of the light source matches with the contour of the target area comprises:
    controlling a part of an area of a liquid crystal display panel to be displayed transparently and other parts of the area of the liquid crystal display panel to be displayed in black, wherein the transparently displayed area corresponds to an area within the contour of the target area.

11. The method according to claim 9, wherein recognizing, by the image recognition module, the contour of the target area and providing the contour of the target area to the optical switch element comprises:
    acquiring, by a first image acquisition module, a first image comprising the target area; and
    recognizing, by an image processing module, the target area from the first image, determining the contour of the target area and providing the contour of the target area to the optical switch element.

12. The method according to claim 11, wherein after controlling, by the optical switch element, the light source, so that the contour of the irradiation area of the light source matches with the contour of the target area, the method further comprises:
    emitting, by the light source, visible light;
    acquiring, by the first image acquisition module, a second image comprising the irradiation area and the target area, and
    recognizing, by the image processing module, the irradiation area from the second image, determining the contour of the irradiation area, recognizing the target area, determining the contour of the target area, and comparing a position of the contour of the target area with a position of the contour of the irradiation area to determine whether they correspond to each other, and if not, adjusting the optical switch element to control the contour of the irradiation area to match with the contour of the target area according to the position of the contour of the target area and the position of the contour of the irradiation area.

13. The method according to claim 11, wherein after controlling, by the optical switch element, the light source, so that the contour of the irradiation area of the light source matches with the contour of the target area, the method further comprises:
    acquiring, by a second image acquisition module, a third image comprising the irradiation area;
    acquiring, by the first image acquisition module, a fourth image currently comprising the target area; and
    recognizing, by the image processing module, the irradiation area from the third image, determining the contour of the irradiation area, recognizing the target area from the fourth image, determining the contour of the target area, comparing the contour of the target area with the contour of the irradiation area to determine whether they match with each other, and if not, adjusting the optical switch element to control the contour of the irradiation area to match with the contour of the target area.

* * * * *